United States Patent [19]

Springolo et al.

[11] Patent Number: 4,861,599
[45] Date of Patent: Aug. 29, 1989

[54] GALENIC FORMULATIONS FOR ORAL USE OF RHEIN DERIVATIVES WITH DELAYED RELEASE FOR THERAPEUTICAL USE

[75] Inventors: Vanna Springolo; Germano Coppi; Mario E. Scevola, all of Milan, Italy

[73] Assignee: Proter S.p.A., Milan, Italy

[21] Appl. No.: 102,936

[22] Filed: Sep. 30, 1987

[30] Foreign Application Priority Data

Oct. 1, 1986 [IT]  Italy .................... 21867 A/86

[51] Int. Cl.$^4$ .............................................. A61K 9/16
[52] U.S. Cl. ................................. 424/494; 424/489; 424/490; 424/493; 424/495; 424/497; 424/456
[58] Field of Search ............... 424/489, 490, 494, 495, 424/497, 493

[56] References Cited

U.S. PATENT DOCUMENTS 4,666,703  5/1987  Kopf .................................. 424/470

Primary Examiner—Thurman K. Page
Attorney, Agent, or Firm—Cushman, Darby & Cushman

[57] ABSTRACT

Several methods are disclosed for the preparation of oral pharmaceutical forms with delayed release of rhein and its derivatives. The pharmaceutically active ingredient is provided in the form of granules, coated with at least one of polyvinylpyrrolidone, shellac and hydroxypropylmethyl cellulose. The desired effect of the coating is to slow release of the pharmaceutically active ingredient by resisting gastric juices in the stomach, but gradually dissolving in the intestines.

2 Claims, 1 Drawing Sheet

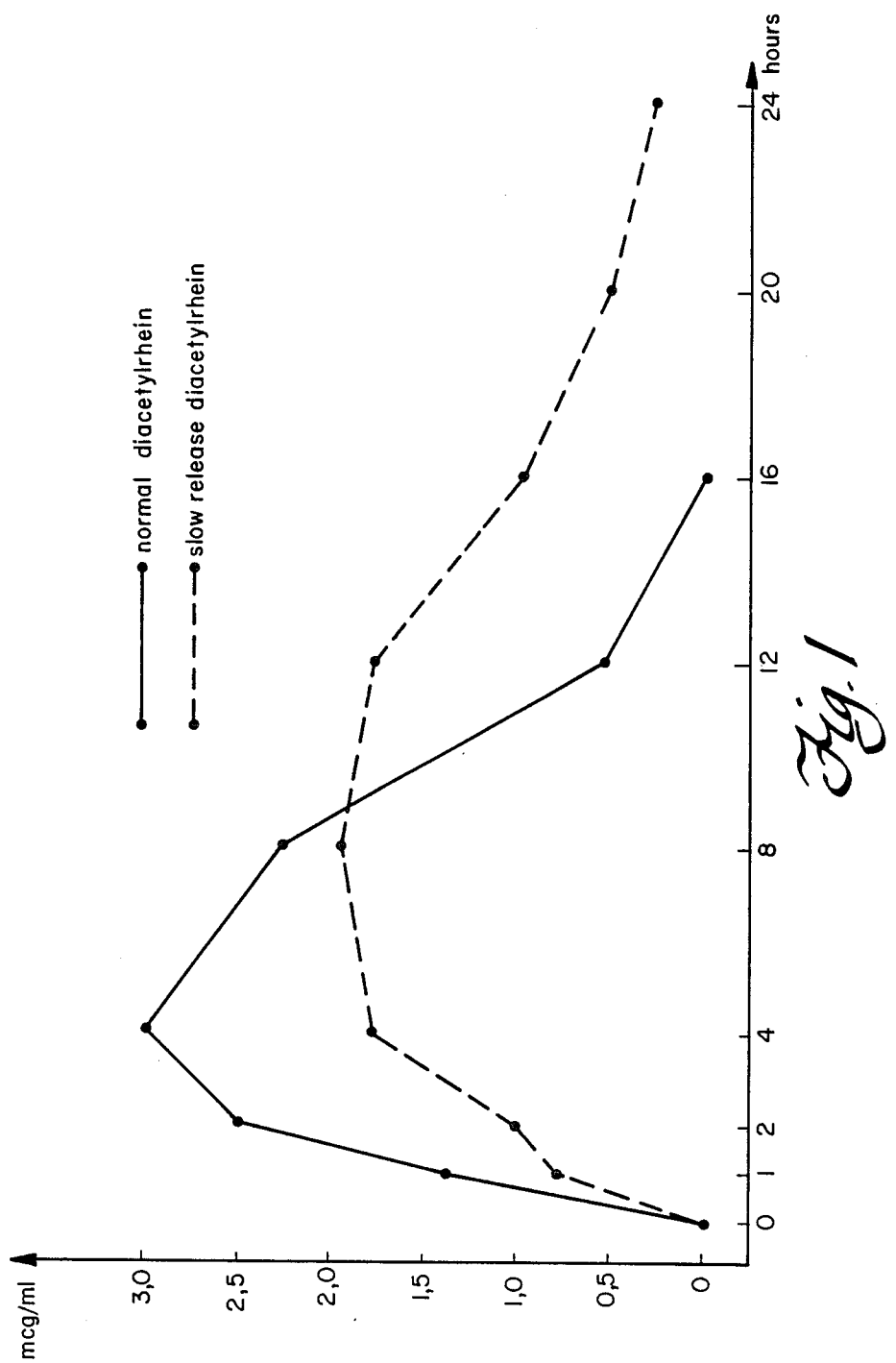

GALENIC FORMULATIONS FOR ORAL USE OF RHEIN DERIVATIVES WITH DELAYED RELEASE FOR THERAPEUTICAL USE

BACKGROUND OF THE INVENTION

The derivatives of rhein of particularly of diacetylrhein are drugs endowed with a relevant antiarthrosic, analgesic and anti-inflammatory activity (Italian Patent No. 1098332).

The present invention relates to a number of formulations for oral use with slow release of dyacetylrhein and other derivatives of rhein for therapeutical purposes.

It is known that the more widespread solid pharmaceutical forms for oral use with delayed release of active ingredients may be reconducted to the following schemes:

(a) comminution of the drug in particles of very small size by supporting them onto nuclei of inert substances. The microgranules thus obtained are thereafter coated with particular excipients (fatty substances and natural or synthetic waxes, plastic substances, etc.) so as to afford to the microgranules different rates of drug release.

(b) Absorption of the drug onto suitable supports, (polymers, synthetic resins, etc.) so as to obtain insoluble complexes from which the active principle is gradually and slowly eluted under the action of the several biological factors of the gastro-enteric tract, such as pH, enzymatic activities, electrolytic concentration, etc.

(c) Supporting onto an inert matrix capable of slowly swelling within the gastro-enteric duct (chemically modified celluloses, polysaccharides, etc.) thus permitting the release of the drug in a gradual manner by diffusion.

(d) Mixed technologies among those listed above which permit, as well, the delayed release of the drug.

SUMMARY OF THE INVENTION

The present invention relate to the preparation of rhein derivatives and particularly of dyacetylrhein derivatives in pharmaceutical formulations which permit a gradual and programmed release of the drug and such as to ensure a pharmacologically active hematic level throughout the period of 24 hours from the administration of the therapeutical dose of the drug.

BRIEF DESCRIPTION OF THE DRAWING

In the Drawing

The FIGURE is a plot comparing level of a therapeutically-active ingredient, over a twenty-four hour period of time, in blood samples, comparing a convention composition with one prepared in accordance with the present invention.

DETAILED DESCRIPTION

Some examples of formulation of rhein derivatives with slow release of the drug are hereinafter described, which have been controlled by an in vitro release test, as well as by determining the hematic levels of the drug after experimental administration to animals.

The examples hereinafter reported are not limiting and are described for the sole purpose of better illustrating the content of the present invention.

EXAMPLE 1

500 g of dyacetylrhein with granule size of between 50 and 100 μum are carefully admixed with 150 g of finely powdered saccharose and 150 g of cornstarch; the mixture is finely ground and then supported onto 1000 g of micronuclei having about 0.4 mm of diameter by wetting with a solution containing 37.5 of polyvinylpyrrolidone. The granulate is dried in a hot air oven, the dried granulate is sieved to prepare end granules of uniform size which are, in portions, coated in a basin with a 20% polyvinyl pyrrolidone and 30% shellac solution isopropanol.

The number of applications of the coating solution onto the several portion of the granules is adjusted as a function of the release times as experimentally measured by means of the in vitro test.

The granules with different coating degrees are admixed as a function of the related release times measured so as to obtain in the same posologic unit (for example a capsule of hard gelatin) the desired amount of drug (for example 100 mg) and the release of the active principle within the programmed times (for instance 24 hours).

EXAMPLE 2

150 g of dipropionylrhein are uniformly admixed with 300 g of lactose, 5 g of dispersed slicon dioxide, 15 g of magnesium stearate, 20 g of talc. Separately, 350 g of dipropionylrhein are carefully admixed with 350 g of titanium dioxide, 115 g of polyvinylpyrrolidone and 25 g of triacetin. This mixture is wetted until a granulate is obtained which is dried in a hot air oven. The granules are coated in portions into a basin with an acetone solution of cellulose acetophtalate by adjusting the number of applications as a function of the release time to be obtained.

The mixture of the powders and the granulates with different coating degree are, in turn, admixed as a function of the related release times as determined in an in vitro test so as to obtain in the same posologic unit (for instance gelatin capsules, tablets, granulates, etc.) the desired amount of drug and the release of the active principle within the programmed time.

EXAMPLE 3

500 g of diacetylrhein are carefully admixed with 10 g of polyvinylpyrrolidone, 50 g of microcrystalline cellulose, 100 g of sodium citrate; the mixture is wet granulated with water and the granulate is dried in a hot air oven.

Separately, 125 g of soya polisaccharides, 10 g of talc and 150 g of magnesium stearate are admixed and the mixture is wet granulated and dried. The two combined granulates are converted into tablets by means of a pressing machine and resulting tablets are coated by subsequent application of ethanol solution containing 40 g of hydroxypropyl-methyl-cellulose, phtalate, 10 g of acetylated monoglyceride and 10 g of titanium dioxide.

"In vitro" release

The capsules obtained according to examples 1 and 3 are tested by means of an in vitro release test according to the method reported in U.S.P. XXI.

| Active principle/ | Percent of released active principle | | | | |
| --- | --- | --- | --- | --- | --- |
| /capsules mg 100 | 1 h | 4 h | 8 h | 18 h | 24 h |
| example No. 1 | 46.4 | 63.1 | 72.7 | 79.3 | 88.7 |
| example No. 3 | 40.7 | 46.7 | 54.7 | 68.5 | 80.3 |

In "vivo" release

As an example the comparison between slow release diacetylrhein prepared according to Example 1 and diacetylrhein in a formulation with immediate release, administered to four male Beagle dogs having an average weight of 10 kg, fasted for about 16 hours before the test, is reported.

The diacetylrhein has been administered in the two pharmaceutical forms according to a "cross-over" experimental scheme at the dose of 20 ml/kg and with a washout time of a week.

The blood sampling has been carried out at the time 0 (basal) and after 1, 2, 4, 8, 12, 16, 20 and 20 hours after the treatment.

In the serum samples, the rhein has been dosed by means of H.P.L.C.. The data reported in the Figure demonstrate that the slow release formulation, while it does not essentially modify the bioavailability ($AUC_{0-24h}$) of diacetylrhein with respect to that of normal formulation, causes, on the contrary, a favourable change of the profile of the serum levels by extending the time of drug permanence in the hematic flow at therapeutical levels up to 24 hours.

We claim:

1. A pharmaceutical composition containing a pharmaceutically active ingredient selected from the group consisting of rhein, diacetylrhein and dipropionylrhein in the form of granules, said granules being coated with a film containing at least one ingredient selected from the group consisting of polyvinylpyrrolidone, shellac, hydroxypropylmethyl cellulose.

2. The pharmaceutical composition of claim 1, wherein:
said film is a multiple-layer film.

* * * * *